United States Patent
Hiraoka et al.

(10) Patent No.: US 9,573,127 B2
(45) Date of Patent: Feb. 21, 2017

(54) PROCESS FOR PRODUCING SHAPED CATALYST AND PROCESS FOR PRODUCING DIENE OR UNSATURATED ALDEHYDE AND/OR UNSATURATED CARBOXYLIC ACID USING THE SHAPED CATALYST

(71) Applicant: NipponKayaku KabushikiKaisha, Tokyo (JP)

(72) Inventors: Ryota Hiraoka, Yamaguchi (JP); Yumi Hino, Yamaguchi (JP); Kimito Okumura, Tokyo (JP); Motohiko Sugiyama, Yamaguchi (JP); Hiroki Motomura, Yamaguchi (JP)

(73) Assignee: NipponKayaku KabushikiKaisha, Tokyo (JP)

( * ) Notice: Subject to any disclaimer, the term of this patent is extended or adjusted under 35 U.S.C. 154(b) by 0 days.

(21) Appl. No.: 14/396,478

(22) PCT Filed: Apr. 19, 2013

(86) PCT No.: PCT/JP2013/061624
§ 371 (c)(1),
(2) Date: Oct. 23, 2014

(87) PCT Pub. No.: WO2013/161703
PCT Pub. Date: Oct. 31, 2013

(65) Prior Publication Data
US 2015/0126774 A1 May 7, 2015

(30) Foreign Application Priority Data

Apr. 23, 2012 (JP) .................................. 2012-098259

(51) Int. Cl.
| | | |
|---|---|---|
| *B01J 23/887* | (2006.01) | |
| *B01J 35/02* | (2006.01) | |
| *B01J 37/02* | (2006.01) | |
| *C07C 45/35* | (2006.01) | |
| *C07C 51/25* | (2006.01) | |
| *C07C 5/48* | (2006.01) | |
| *B01J 23/88* | (2006.01) | |
| *B01J 37/03* | (2006.01) | |
| *B01J 37/00* | (2006.01) | |

(52) U.S. Cl.
CPC ........... *B01J 37/0223* (2013.01); *B01J 23/88* (2013.01); *B01J 23/8876* (2013.01); *B01J 35/026* (2013.01); *B01J 37/0045* (2013.01); *B01J 37/038* (2013.01); *C07C 5/48* (2013.01); *C07C 45/35* (2013.01); *C07C 51/252* (2013.01); *B01J 2523/00* (2013.01); *C07C 2523/04* (2013.01); *C07C 2523/28* (2013.01); *C07C 2523/745* (2013.01); *C07C 2523/75* (2013.01); *C07C 2523/755* (2013.01); *C07C 2523/88* (2013.01); *C07C 2523/883* (2013.01); *C07C 2523/887* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 4,419,267 | A | 12/1983 | Sasaki et al. |
| 5,072,052 | A | 12/1991 | Boeck et al. |
| 6,028,220 | A | 2/2000 | Wada et al. |
| 6,509,508 | B2 | 1/2003 | Kimura et al. |
| 6,740,769 | B1 | 5/2004 | Mizutani et al. |
| 6,781,013 | B2 | 8/2004 | Tanimoto |
| 6,784,134 | B2 | 8/2004 | Kasuga et al. |
| 6,878,847 | B2 | 4/2005 | Kasuga et al. |
| 2005/0239643 | A1 | 10/2005 | Benderly et al. |
| 2011/0034330 | A1 | 2/2011 | Czaja et al. |
| 2011/0144406 | A1 | 6/2011 | Masatsugu et al. |
| 2012/0130137 | A1 | 5/2012 | Orita et al. |
| 2013/0172615 | A1 | 7/2013 | Kawano et al. |
| 2015/0328623 | A1 | 11/2015 | Hiraoka et al. |

FOREIGN PATENT DOCUMENTS

| | | |
|---|---|---|
| CA | 903079 A | 6/1972 |
| CN | 1050181 A | 3/1991 |
| CN | 101990460 A | 3/2011 |
| EP | 2298446 A1 | 3/2011 |
| EP | 2617491 A1 | 7/2013 |
| EP | 2842625 A1 | 3/2015 |
| EP | 2842626 A1 | 3/2015 |
| JP | 43-27742 B | 11/1968 |
| JP | 49-3498 B | 1/1974 |

(Continued)

OTHER PUBLICATIONS

Chinese communication, with English translation, dated Apr. 12, 2016 in co-pending Chinese patent application No. 201380021493.0.

(Continued)

*Primary Examiner* — Colin W Slifka
(74) *Attorney, Agent, or Firm* — Nields, Lemack & Frame, LLC

(57) ABSTRACT

There is provided a process for producing a shaped catalyst for a fixed bed oxidation reaction or a fixed bed oxidative dehydrogenation reaction, the catalyst having both of sufficient mechanical strength and catalyst performance, and the catalyst is produced by supporting a catalyst powder containing a complex metal oxide having molybdenum as an essential ingredient on an inert support by a tumbling granulation method at a relative centrifugal force of 1 to 35 G.

4 Claims, No Drawings

(56) References Cited

FOREIGN PATENT DOCUMENTS

| | | | |
|---|---|---|---|
| JP | 56-163756 | A | 12/1981 |
| JP | 58-188823 | A | 11/1983 |
| JP | 3775872 | B | 5/2006 |
| JP | 2011-518659 | A | 6/2011 |
| JP | 2011-178719 | A | 9/2011 |
| JP | 2011-219366 | A | 11/2011 |
| JP | 2011-246384 | A | 12/2011 |
| JP | 2012-45516 | A | 3/2012 |
| JP | 5130562 | B | 1/2013 |
| KR | 1019990077024 | A | 10/1999 |
| KR | 1020120026049 | A | 3/2012 |
| TW | 200539939 | A | 12/2005 |
| TW | 201100372 | A | 1/2011 |
| WO | 2012036038 | A1 | 3/2012 |
| WO | 2015053269 | A1 | 4/2015 |

OTHER PUBLICATIONS

Chinese communication, with English translation, dated Aug. 25, 2015 in corresponding Chinese patent application No. 201380021431.X.

International Search Report and Written Opinion mailed May 21, 2013 in corresponding PCT application No. PCT/J132013/061624.

International Preliminary Report on Patentability mailed Nov. 6, 2014 in corresponding PCT application No. PCT/J132013/061624.

International Search Report and Written Opinion mailed May 21, 2013 in co-pending PCT application No. PCT/JP2013/061623.

International Preliminary Report on Patentability mailed Nov. 6, 2014 in co-pending PCT application No. PCT/JP2013/061623.

European communication dated Sep. 24, 2015 in corresponding European patent application No. 13782624.4.

European communication dated Sep. 24, 2015 in co-pending European patent application No. 13782374.6.

Sommer, et al., "Auslegung von Granulierteller and Granuliertrommel", Chemie Ingenieur Technik, vol. 50, No. 7, Jan. 1, 1978, p. 518-524.

Saudi Arabian communication, with English translation, dated Aug. 9, 2015 in corresponding Saudi Arabian patent application No. 11340492.

Japanese communication, with English translation, dated Jan. 26, 2016 in corresponding Japanese patent application No. 2014-512523.

Taiwanese communication, with English translation, dated Jan. 26, 2016 in corresponding Taiwanese patent application No. 102114342.

Office action mailed Apr. 14, 2016 in co-pending U.S. Appl. No. 14/396,483.

Saudi Arabian communication, with English translation, dated May 6, 2015 in corresponding Saudi Arabian patent application No. 113340492.

Office action mailed Jun. 28, 2016 in co-pending U.S. Appl. No. 14/396,483.

Taiwanese communication, with English translation, dated Jul. 1, 2016 in corresponding Taiwanese patent application No. 102114335.

Korean communication, with English translation, dated Nov. 17, 2016 in corresponding Korean patent application No. 10-2014-7029775.

PROCESS FOR PRODUCING SHAPED CATALYST AND PROCESS FOR PRODUCING DIENE OR UNSATURATED ALDEHYDE AND/OR UNSATURATED CARBOXYLIC ACID USING THE SHAPED CATALYST

TECHNICAL FIELD

The present invention relates to a process for producing a shaped catalyst used in the production of a diene or an unsaturated aldehyde and/or an unsaturated carboxylic acid.

BACKGROUND ART

Unsaturated carboxylic acids such as acrylic acid and methacrylic acid used as raw materials for various chemicals can be produced by a two-stage reaction using unsaturated aldehydes as intermediate products. Since a demand for both of acrylic acid and methacrylic acid continues to increase steadily, efforts have been intensively made at improving catalysts used in the production thereof.

On the other hand, a demand for butadiene, which is an important raw material for chemicals to be used as a raw material for synthetic rubbers and the like, has steeply increased as a raw material for energy-saving type automobile tires owing to global augmentation in demand for automobiles and increase in awareness of environmental issues in recent years. However, since the production of C4 fractions has decreased, the shortage of butadiene production has continued. Thus, it is forecasted that the shortage of butadiene supply should be further accelerated hereafter. Therefore, it has been strongly desired to industrialize a novel process for producing butadiene.

A process for producing an unsaturated aldehyde and/or an unsaturated carboxylic acid by a selective oxidation reaction of an unsaturated hydrocarbon in a fixed bed reaction apparatus with a complex metal oxide catalyst having molybdenum as an essential ingredient has been well known. Moreover, a process for producing butadiene from n-butene in a fixed bed reaction apparatus using a complex metal oxide catalyst having molybdenum as an essential ingredient has been also well known.

The shape of the catalyst for use in the fixed bed reaction apparatus is selected depending on its use but catalyst shapes such as a ring shape, a cylinder shape, a tablet shape, a honeycomb shape, a trefoil shape, a quatrefoil shape, and a spherical one have been frequently used. Of these, a spherical catalyst has been widely used due to easiness of an operation of packing the catalyst into a reaction tube and an operation of extracting the catalyst after use from the reaction tube.

Moreover, a method of supporting a catalyst-active ingredient on an inert support has been industrially widely used to produce the supported catalyst for the purpose of suppressing a decrease in selectivity for a target product by a successive reaction and reducing heat accumulation in a catalyst layer in a reaction in which heat generation is involved. Particularly, in the case where a target product is selectively produced by an oxidation reaction or an oxidative dehydrogenation reaction of an organic compound, the supported catalyst is used as an effective method.

As a process for producing a spherical supported shaped catalyst, Patent Document 1 discloses a process for producing a catalyst for producing acrolein and/or acrylic acid from propylene and Patent Document 2 discloses a process for producing a catalyst for producing methacrolein and/or methacrylic acid from isobutylene and/or tertiary-butyl alcohol.

In Patent Documents 1 and 2, as a process for producing a spherical shaped catalyst, a production process by a tumbling granulation method is disclosed. Specifically, a spherical support necessary for attaining a desired catalyst diameter is placed in a tumbling granulation apparatus and a liquid as a binder and a catalyst-active ingredient and/or a precursor thereof are sprinkled on the support with rotating the shaping machine, thereby producing the spherical shaped catalyst.

As mentioned above, a process for producing butadiene from n-butene is known. For example, in Patent Documents 3 and 4, processes of oxidative dehydrogenation in the presence of a complex metal oxide catalyst containing molybdenum, bismuth, iron, and cobalt as main ingredients have been described. However, from the standpoints of catalyst activity, butadiene selectivity, stability of reaction operation, catalyst life, catalyst production, and the like, conventional catalysts are industrially insufficient and an improvement thereof has been strongly desired.

Moreover, in Patent Document 5, there is a description of a supported catalyst that is produced in the presence of a pore-forming agent and a production thereof in an industrial scale is also described.

BACKGROUND ART DOCUMENT

Patent Document

[Patent Document 1] Japanese Patent No. 3775872
[Patent Document 2] Japanese Patent No. 5130562
[Patent Document 3] JP-B-49-003498
[Patent Document 4] JP-A-58-188823
[Patent Document 5] JP-A-2011-518659

SUMMARY OF INVENTION

Problem that Invention is to Solve

However, in Patent Document 5, an effect on conversion of butene and selectivity for butadiene attributable to the production of the supported catalyst in the presence of the pore-forming agent is not clearly shown. Moreover, in the production process of the supported catalyst cited in Patent Document 5, conditions in which relative centrifugal force is extremely low as compared with the process of the present invention are employed and thus the production process is practically problematic in view of mechanical strength of the catalyst.

An object of the present invention is to provide a process for producing a shaped catalyst having both of sufficient mechanical strength and catalytic performance.

Means for Solving Problem

As a result of extensive studies, the present inventors have found that a catalyst produced with imparting a specific relative centrifugal force by controlling the diameter (rotation radius) and rotation speed of a tumbling granulator in the production step of the shaped catalyst is a catalyst having both of a high catalytic performance and a strong mechanical strength. Thus, they have accomplished the invention.

Namely, the invention relates to the followings.

[1] A process for producing a shaped catalyst for a fixed-bed oxidation reaction or a fixed-bed oxidative dehydrogenation reaction, comprising:

supporting a catalyst powder containing a complex metal oxide having molybdenum as an essential ingredient on an inert support by a tumbling granulation method at a relative centrifugal force of 1 to 35 G.

[2] The process for producing a shaped catalyst as described in [1] above, wherein the complex metal oxide has a composition represented by the following formula (1):

$$Mo_a Bi_b Ni_c Co_d Fe_f X_g Y_h O_x \quad \text{Formula (1)}$$

wherein Mo, Bi, Ni, Co, Fe and O represents molybdenum, bismuth, nickel, cobalt, iron and oxygen, respectively;

X represents at least one element selected from the group consisting of tungsten, antimony, tin, zinc, chromium, manganese, magnesium, silicon, aluminum, cerium, tellurium, boron, germanium, zirconium and titanium;

Y represents at least one element selected from the group consisting of potassium, rubidium, calcium, barium, thallium and cesium;

a, b, c, d, f, g, h and x represents numbers of atoms of molybdenum, bismuth, nickel, cobalt, iron, X, Y and oxygen, respectively, and a=12, b=0.1 to 7, c+d=0.5 to 20, f=0.5 to 8, g=0 to 2, h=0.005 to 2, and x=a value determined depending on oxidation states of individual elements.

[3] The process for producing a shaped catalyst as described in [1] or [2] above, wherein an attrition degree of the shaped catalyst to be produced is 3% by weight or less.

[4] The process for producing a shaped catalyst as described in any one of [1] to [3] above, wherein the shaped catalyst to be produced is a catalyst used in a reaction of producing butadiene from n-butene by an oxidative dehydrogenation reaction.

[5] A process for producing butadiene, comprising:

oxidatively dehydrogenating n-butene into butadiene by a gas-phase contact oxidative dehydrogenation reaction in a presence of molecular oxygen using the shaped catalyst obtained by the production process as described in [4] above.

[6] The process for producing a shaped catalyst as described in any one of [1] to [3] above, wherein the shaped catalyst to be produced is a catalyst used in a reaction of producing an unsaturated aldehyde and/or an unsaturated carboxylic acid from an unsaturated hydrocarbon by an oxidation reaction.

[7] A process for producing an unsaturated aldehyde and/or unsaturated carboxylic acid, comprising:

oxidizing an unsaturated hydrocarbon into a corresponding unsaturated aldehyde and/or unsaturated carboxylic acid by a gas-phase contact oxidation reaction in a presence of molecular oxygen using the shaped catalyst obtained by the production process as described in [6] above.

Effects of Invention

According to the invention, it is possible to produce a shaped catalyst having both of sufficient mechanical strength and catalytic performance.

MODE FOR CARRYING OUT INVENTION

The following will describe embodiments according to the process of the invention.

In the following, description is made using, as an example, a catalyst having molybdenum-bismuth as principal active ingredients for producing acrolein and/or acrylic acid from propylene, methacrolein and/or methacrylic acid from isobutylene and/or tertiary-butyl alcohol, or butadiene from n-butene, which are preferable uses of the shaped catalyst obtained by the production process of the invention.

With regard to the complex metal oxide contained in the catalyst powder in the shaped catalyst obtained in the invention, as far as molybdenum is contained as an essential element, the other constituent elements and a composition ratio thereof are not particularly limited but the complex metal oxide can be preferably represented by the following general formula (1):

$$Mo_a Bi_b Ni_c Co_d Fe_f X_g Y_h O_x \quad \text{Formula (1)}$$

wherein Mo, Bi, Ni, Co, Fe, and O represents molybdenum, bismuth, nickel, cobalt, iron, and oxygen, respectively, X represents at least one element selected from the group consisting of tungsten, antimony, tin, zinc, chromium, manganese, magnesium, silicon, aluminum, cerium, tellurium, boron, germanium, zirconium and titanium, Y represents at least one element selected from the group consisting of potassium, rubidium, calcium, barium, thallium and cesium, a, b, c, d, f, g, h and x represents numbers of atoms of molybdenum, bismuth, nickel, cobalt, iron, X, Y and oxygen, respectively, and a=12, b=0.1 to 7, preferably b=0.5 to 4, c+d=0.5 to 20, preferably c+d=1 to 12, f=0.5 to 8, preferably f=0.5 to 5, g=0 to 2, preferably g=0 to 1, h=0.005 to 2, preferably h=0.01 to 0.5, and x=a value determined depending on the oxidation states of individual elements.

Here, the powder containing the catalyst-active ingredient is prepared by a known method such as a co-precipitation method or a spray drying method. Raw materials used on that occasion are not particularly limited and nitrate salts, ammonium salts, hydroxides, oxides, acetate salts, and the like of various metal elements such as molybdenum, bismuth, nickel, cobalt, iron, X, and Y can be used without particular limitation. It is also possible to obtain the powder containing the catalyst-active ingredient by preparing a liquid or slurry containing different kinds of catalyst-active ingredients by changing the kind and/or amount of the metal salts to be supplied to water and performing a spray drying method or the like.

The catalyst-active ingredient (hereinafter referred to as pre-baked powder) can be obtained by baking the thus obtained powder at 200 to 600° C., preferably 300 to 500° C., preferably in an air or nitrogen stream.

The thus obtained pre-baked powder can be used as a catalyst as it is but, in the invention, is shaped in consideration of production efficiency and workability. The shape of the shaped one is not particularly limited as long as it can be coated with the catalyst ingredient but is preferably a spherical one in view of production and actual use. At shaping, it is common to use and shape a single pre-baked powder. However, separately prepared granular pre-baked powders having different ingredient compositions may be mixed beforehand at any ratio and then shaped or a method of repeating an operation of supporting different kinds of pre-baked powders on an inert support to shape the pre-baked powders as multi-layers may be employed. In this connection, at shaping, it is preferred to mix a shaping aid material such as crystalline cellulose and/or a strength enhancer such as ceramic whisker. The amount of each of the shaping aid and the strength enhancer to be used is preferably 30% by weight or less relative to the amount of the pre-baked powder. Moreover, the shaping aid and/or the strength enhancer may be previously mixed with the pre-baked powder before shaping or may be added simultaneously to or before or after the addition of the pre-baked powder to a shaping machine. Namely, the above shape of the shaped one and shaping method can be adopted as long as the shaped catalyst to be used in the reaction has finally catalyst physical properties and/or catalyst composition falling within the desired ranges.

According to the production process of the invention, a catalyst shaped by the method in which the pre-baked powder (including the shaping aid and the strength enhancer according to need) is coat-shaped on an inert support such as a ceramic can be produced. Namely, as a supporting method, the pre-baked powder is shaped by a tumbling granulation method so that the powder homogeneously coats the surface of the support. At this time, by rotating the shaping machine containing the support charged thereinto at a high speed, the support charged into the vessel is vigorously stirred by repeated rotation movement and orbital movement of the support and rotation of the support itself. In this case, it is preferred to use a method in which the catalyst powder is coat-shaped on the support by adding the pre-baked powder and, if necessary, the molding aid and the strength enhancer.

At supporting, a liquid binder is preferably used.

Specific examples of the usable binder include water, ethanol, methanol, propanol, polyhydric alcohols, polyvinyl alcohol of a polymeric binder, and an aqueous silica sol solution of an inorganic binder. Ethanol, methanol, propanol, and polyhydric alcohols are preferred, diols such as ethylene glycol and triols such as glycerin are more preferred, and an aqueous solution having a glycerin concentration of 5% by weight or more is particularly preferred. When an appropriate amount of the aqueous glycerin solution is used, shapability becomes good and a catalyst having a high mechanical strength and exhibiting a high activity and a high performance is obtained. The amount of the binder to be used is usually in an amount of 2 to 60 parts by weight based on 100 parts by weight of the pre-baked powder and, in the case of the aqueous glycerin solution, the amount is preferably 10 to 50 parts by weight. At supporting, the binder may be added to the tumbling granulator together with the pre-baked powder or the binder and the pre-baked powder may be added thereto alternately.

With regard to the size of the inert support, one having a size of about 2 to 20 mm is usually used and the pre-baked powder is supported thereon. The support ratio is determined in consideration of conditions for using the catalyst, for example, space velocity and concentration of the raw material hydrocarbon.

Usually, it is preferred to support the pre-baked powder so that the support ratio becomes 10 to 80% by weight. The support ratio of the catalyst after shaping is defined by the following formula (2).

Support ratio (%)=(Weight of pre-baked powder/
(Weight of pre-baked powder+Weight of inert
support))×100    Formula (2)

The above relative centrifugal force to be imparted at tumbling granulation is usually 1 G to 35 G, preferably 1.2 G to 30 G, and more preferably 1.5 G to 20 G. Here, the relative centrifugal force is a numerical value represented by the ratio of the intensity of centrifugal force per unit weight to gravitational force at the time when the support is placed in the tumbling granulator and is rotated in the apparatus, and is represented by the following formula (3). The relative centrifugal force increases in proportion to an absolute value of distance from the center of rotation of the apparatus and the square of rotation speed.

RCF=1118×r×$N^2$×$10^{-8}$    Formula (3)

In the formula (3), RCF represents relative centrifugal force (G), r represents distance (cm) from the center of rotation, and N represents rotation speed (rpm).

For shaping, an apparatus having a common size can be used.

In the case where a shaping machine having a small rotation radius is used, the relative centrifugal force can be controlled by increasing the rotation speed. The rotation radius is not particularly limited but, practically, it is convenient to use a commercially available device and the radius is usually preferably about 0.1 to 2 m. The rotation speed is determined depending on the size of the molding machine to be used according to the above formula (3) so that the relative centrifugal force falls within the above range. The amount of the inert support to be charged into the shaping machine is appropriately set depending on the size of the shaping machine, desired production rate, and the like but the production is preferably performed in the range of 0.1 to 100 kg.

Also in Patent Document 5, it is suggested to produce a supported catalyst containing molybdenum by a tumbling granulation method. However, the rotation speed at the tumbling granulation is extremely slow as compared with the process of the invention. Therefore, the relative centrifugal force is also extremely low as compared with the process of the invention.

The shaped catalyst processed through the tumbling granulation step can be packed into a reactor also as it is. However, for the purpose of avoiding a possibility that the catalyst is heated to a high temperature owing to combustion of remaining binder and the like in the catalyst at heating and from the standpoint of securing safety and health at operation and practical strength, the shaped catalyst subjected to the tumbling granulation step is preferably baked again before the catalyst is used in the reaction. The baking temperature at the second baking is 450 to 650° C. and the baking time is 3 to 30 hours, preferably 4 to 15 hours. They are appropriately set depending on the reaction conditions to be used. The atmosphere for the baking may be any of an air atmosphere and a nitrogen atmosphere but, industrially, an air atmosphere is preferred.

The thus obtained catalyst of the invention has a high mechanical strength. Specifically, abrasion degree is preferably 3% by weight or less, more preferably 1.5% by weight or less, and further preferably 0.5% by weight or less.

The thus obtained catalyst of the invention can be used in the step of gas-phase contact oxidation of propylene with molecular oxygen or a molecular oxygen-containing gas to produce acrolein and acrylic acid, in the step of gas-phase contact oxidation of isobutylene or tertiary-butyl alcohol, which is known to be easily converted into isobutylene and water on a solid acid catalyst such as the catalyst of the invention, with molecular oxygen or a molecular oxygen-containing gas to produce methacrolein and methacrylic acid, or in the step of producing butadiene by a gas-phase contact oxidative dehydrogenation reaction of n-butene with molecular oxygen or a molecular oxygen-containing gas. In the production process of the invention, the method for passing through the raw material gas may be a usual single path method or a recycling method and can be carried out under commonly used conditions without particular limitation. For example, the reaction can be performed with introducing a mixed gas composed of propylene as a starting raw material in an amount of 1 to 10% by volume, preferably 4 to 9% by volume at ordinary temperature, molecular oxygen in an amount of 3 to 20% by volume, preferably 4 to 18% by volume, water vapor in an amount of 0 to 60% by volume, preferably 4 to 50% by volume, an inert gas such as carbon dioxide or nitrogen in an amount of 20 to 80% by volume, preferably 30 to 60% by volume onto the catalyst of the invention packed in a reaction tube at 250 to 450° C. under a pressure of ordinary pressure to 10 atm at a space velocity of 300 to 5,000 $h^{-1}$.

In the case of the oxidative dehydrogenation reaction of n-butene, for example, the reaction can be performed with introducing a mixed gas composed of n-butene as a starting raw material in an amount of 1 to 16% by volume, preferably 3 to 12% by volume at ordinary temperature, molecular oxygen in an amount of 1 to 20% by volume, preferably 5 to 16% by volume, water vapor in an amount of 0 to 60% by volume, preferably 4 to 50% by volume, an inert gas such as carbon dioxide or nitrogen in an amount of 64 to 98% by volume, preferably 72 to 92% by volume onto the catalyst of the invention packed in a reaction tube at 250 to 450° C. under a pressure of ordinary pressure to 10 atm at a space velocity of 300 to 5,000 $h^{-1}$.

EXAMPLES

The following will more specifically describe the invention with reference to Examples but the invention should not be construed as being limited to Examples.

Incidentally, the conversion and yield in the invention are each defined as follows.

Conversion of raw material compound (% by mol)= (Number of moles of reacted raw material compound/Number of moles of supplied raw material compound)×100

Yield (% by mol)=(Number of moles of formed target compound/Number of moles of supplied raw material compound)×100

In the calculation formulae, in the case of the oxidation reaction using propylene as the raw material compound, the target compound is "acrolein+acrylic acid". In the case of the oxidation reaction using isobutylene and/or tertiary-butyl alcohol as the raw material compound, the target compound is "methacrolein+methacrylic acid". Moreover, in the case of the oxidative dehydrogenation reaction using n-butene as the raw material compound, the target compound is butadiene.

Example 1

Production of Catalyst

While heating and stirring 3,000 parts by weight of distilled water, 423.8 parts by weight of ammonium molybdate tetrahydrate and 3.0 parts by weight of potassium nitrate were dissolved therein to obtain an aqueous solution (A1). Separately, 302.7 parts by weight of cobalt nitrate hexahydrate, 162.9 parts by weight of nickel nitrate hexahydrate, and 145.4 parts by weight of ferric nitrate nonahydrate were dissolved in 1,000 parts by weight of distilled water to prepare an aqueous solution (B1) and 164.9 parts by weight of bismuth nitrate pentahydrate was dissolved in 200 parts by weight of distilled water, which had been acidified by adding 42 parts by weight of conc. nitric acid, to prepare an aqueous solution (C1). Then, (B1) and (C1) were sequentially mixed into the above aqueous solution (A1) with vigorous stirring and the formed suspension was dried by means of a spray dryer and baked at 440° C. for 6 hours to obtain a pre-baked powder (D1). The composition ratio of the catalyst-active ingredient excluding oxygen at this time was as follows: Mo=12, Bi=1.7, Ni=2.8, Fe=1.8, Co=5.2 and K=0.15 in terms of atomic ratio.

Thereafter, using a powder obtained by mixing 5 parts by weight of crystalline cellulose into 100 parts by weight of the pre-baked powder and an inert support (a spherical material containing alumina and silica as main ingredients and having a diameter of 4.5 mm), the weight of the support and the weight of the pre-baked powder to be used for shaping were adjusted so that the support ratio defined by the above formula (2) became 50% by weight. Using a 20% by weight aqueous glycerin solution as a binder, a shaped catalyst (E1) was obtained by supporting and shaping into a spherical shape having a diameter of 5.2 mm.

For supporting and shaping, using a cylindrical shaping machine having a diameter of 23 cm, the rotation speed of the bottom plate was set at 150 rpm. The relative centrifugal force at this time was 2.9 G.

The shaped catalyst (E1) was baked at a baking temperature of 510° C. for 4 hours under an air atmosphere to obtain a shaped catalyst (F1).

(Oxidation Reaction Test)

The shaped catalyst (F1) was packed in an amount of 68 ml into a stainless steel-made reaction tube having an inner diameter of 28.4 mm in which the thermocouple to measure the catalyst layer temperature was installed and then the reaction tube being fitted into the reactor with a bath of fluidizing alumina powder as a heat transfer medium using air. The temperature of the reaction bath was set at 320° C. A gas was introduced into the reaction tube at a space velocity of 862 $h^{-1}$, the gas in which the supply amounts of propylene, air, and water were set so that the molar ratio of the raw materials became as follows: propylene:oxygen:nitrogen:water=1:1.7:6.4:3.0. Then, catalyst performance was evaluated after 20 hours from the beginning of the reaction with controlling the pressure at reactor outlet to 0 kPaG. Table 1 shows the results.

(Strength Measurement)

The shaped catalyst (F1) was charged in an amount of 50.0 g into a cylindrical rotating machine having a radius of 14 cm, the machine being fitted with one baffle plate inside, and the machine was rotated at 23 rpm for 10 minutes. Thereafter, the powder rubbed off was removed by a sieve with 1.7 mm opening aperture, the amount of the remaining catalyst was measured, and attrition degree was determined from the following formula. Table 1 shows the results.

Attrition Degree (%)=(50.0−Amount of remaining catalyst)/50.0×100

Example 2

A shaped catalyst (F2) was produced in the same manner as in Example 1 except that the rotation speed of the bottom plate was set at 210 rpm and the relative centrifugal force was set at 5.7 G at shaping. Table 1 shows the results of the oxidation reaction test and the results of the strength measurement of the shaped catalyst (F2).

Example 3

A shaped catalyst (F3) was produced in the same manner as in Example 1 except that the rotation speed of the bottom plate was set at 260 rpm and the relative centrifugal force was set at 8.7 G at shaping. Table 1 shows the results of the oxidation reaction test and the results of the strength measurement of the shaped catalyst (F3).

Example 4

A shaped catalyst (F4) was produced in the same manner as in Example 1 except that the rotation speed of the bottom plate was set at 430 rpm and the relative centrifugal force was set at 24 G at shaping. Table 1 shows the results of the oxidation reaction test and the results of the strength measurement of the shaped catalyst (F4).

Comparative Example 1

A shaped catalyst (V1) was produced in the same manner as in Example 1 except that the rotation speed of the bottom plate was set at 75 rpm and the relative centrifugal force was set at 0.72 G at shaping. Table 1 shows the results of the oxidation reaction test and the results of the strength measurement of the shaped catalyst (V1).

Example 5

Production of Catalyst

While heating and stirring 12,000 parts by weight of distilled water, 3,000 parts by weight of ammonium molybdate tetrahydrate and 55.2 parts by weight of cesium nitrate were dissolved therein to obtain an aqueous solution (A2). Separately, 2,782 parts by weight of cobalt nitrate hexahydrate, 1,144 parts by weight of ferric nitrate nonahydrate, and 412 parts by weight of nickel nitrate hexahydrate were dissolved in 2,300 parts by weight of distilled water to prepare an aqueous solution (B2) and 1,167 parts by weight of bismuth nitrate pentahydrate was dissolved in 1,215 parts by weight of distilled water, which had been acidified by adding 397 parts by weight of conc. nitric acid, to prepare an aqueous solution (C2). Then, (B2) and (C2) were sequentially mixed into the above aqueous solution (A2) with vigorous stirring of the aqueous solution (A2), the formed suspension was dried by means of a spray dryer, and the resulting powder was baked at 460° C. for 5 hours to obtain a pre-baked powder (D2). The composition ratio of the catalyst-active ingredient excluding oxygen at this time was as follows: Mo=12, Bi=1.7, Fe=2.0, Co=6.75, Ni=1.0 and Cs=0.20 in terms of atomic ratio.

Thereafter, using a powder obtained by mixing 5 parts by weight of crystalline cellulose into 100 parts by weight of the pre-baked powder and an inert support (a spherical material containing alumina and silica as main ingredients and having a diameter of 4.5 mm), the weight of the support and the weight of the pre-baked powder to be used for shaping were adjusted so that the support ratio defined by the above formula (2) became 50% by weight. Using a 20% by weight aqueous glycerin solution as a binder, a shaped catalyst (E5) was obtained by supporting and shaping into a spherical shape having a diameter of 5.2 mm.

For supporting and shaping, using a cylindrical shaping machine having a diameter of 23 cm, the rotation speed of the bottom plate was set at 260 rpm. The relative centrifugal force at this time was 8.7 G.

The shaped catalyst (E5) was baked at a baking temperature of 500° C. for 4 hours under an air atmosphere to obtain a shaped catalyst (F5).

(Oxidation Reaction Test)

The shaped catalyst (F5) was packed in an amount of 34 ml into a stainless steel-made reaction tube having an inner diameter of 22 mm in which the thermocouple to measure the catalyst layer temperature was installed and then the reaction tube being fitted into the reactor with a bath of fluidizing alumina powder as a heat transfer medium using air. The temperature of the reaction bath was set at 350° C. A gas was introduced into the reaction tube at a space velocity of 1,200 $h^{-1}$, the gas in which the supply amounts of isobutylene, air, water, and nitrogen were set so that the molar ratio of the raw materials became as follows: isobutylene:oxygen:nitrogen:water=1:2.2:12.5:1.0. Then, catalyst performance was evaluated after 20 hours from the beginning of the reaction with controlling the pressure at reactor outlet to 0.5 kPaG. Table 1 shows the results.

(Strength Measurement)

The attrition degree was determined in the same manner as in Example 1. Table 1 shows the results.

Example 6

A shaped catalyst (F6) was produced in the same manner as in Example 5 except that the rotation speed at shaping was set at 430 rpm and the relative centrifugal force was set at 23.8 G. Table 1 shows the results of the oxidation reaction test and the results of the strength measurement of the shaped catalyst (F6).

Example 7

Production of Catalyst

A shaped catalyst (F7) was produced in the same manner as in Example 5 except that the rotation speed at shaping was set at 260 rpm and the relative centrifugal force was set at 8.7 G. Table 1 shows the results of the oxidative dehydrogenation reaction test of the shaped catalyst (F7) performed by the method described below and the results of the strength measurement thereof.

(Oxidative Dehydrogenation Reaction Test)

The shaped catalyst (F7) was packed in an amount of 53 ml into a stainless steel-made reaction tube having an inner diameter of 28.4 mm in which the thermocouple to measure the catalyst layer temperature was installed and then the reaction tube being fitted into the reactor with a bath of fluidizing alumina powder as a heat transfer medium using air. The temperature of the reaction bath was set at 340° C. A gas was introduced into the reaction tube at a space velocity of 1,440 $h^{-1}$, the gas in which the supply amounts of 1-butene, air, water, and nitrogen were set so that the molar ratio of the raw materials became as follows: 1-butene:oxygen:nitrogen:water=1:2.1:10.4:2.5. Then, catalyst performance was evaluated after 15 hours from the beginning of the reaction with controlling the pressure at reactor outlet to 0 kPaG.

Example 8

A shaped catalyst (F8) was produced in the same manner as in Example 7 except that the rotation speed at shaping was set at 430 rpm and the relative centrifugal force was set at 23.8 G. Table 1 shows the results of the oxidative dehydrogenation reaction test performed in the same manner as in Example 7 and the results of the strength measurement using the shaped catalyst (F8).

Comparative Example 2

A shaped catalyst (V2) was produced in the same manner as in Example 7 except that the rotation speed at shaping was set at 550 rpm and the relative centrifugal force was set at 38.9 G. Table 1 shows the results of the oxidative dehydrogenation reaction test performed in the same manner as in Example 7 and the results of the strength measurement using the shaped catalyst (V2).

Comparative Example 3

A shaped catalyst (V3) was produced in the same manner as in Example 7 except that the rotation speed at shaping was set at 60 rpm and the relative centrifugal force was set at 0.46 G. Table 1 shows the results of the oxidative dehydrogenation reaction test performed in the same manner as in Example 7 and the results of the strength measurement using the shaped catalyst (V3).

TABLE 1

Results of Catalytic Reaction and Attrition Degree

| Example | Catalyst Name | Relative centrifugal force (G) | Attrition degree (%) | Raw material compound | Conversion of raw material (%) | Yield (%) |
|---|---|---|---|---|---|---|
| Example 1 | F1 | 2.9 | 0.40 | propylene | 97.1 | 90.5 |
| Example 2 | F2 | 5.7 | 0.25 | propylene | 97.4 | 90.0 |
| Example 3 | F3 | 8.7 | 0.36 | propylene | 97.4 | 89.6 |
| Example 4 | F4 | 23.8 | 1.07 | propylene | 97.5 | 90.7 |
| Comparative Example 1 | V1 | 0.72 | 3.75 | propylene | 97.1 | 91.3 |
| Example 5 | F5 | 8.7 | 0.20 | isobutylene | 99.6 | 77.6 |
| Example 6 | F6 | 23.8 | 0.24 | isobutylene | 99.3 | 78.5 |
| Example 7 | F7 | 8.7 | 0.05 | 1-butene | 97.9 | 89.9 |
| Example 8 | F8 | 23.8 | 0.24 | 1-butene | 97.9 | 90.1 |
| Comparative Example 2 | V2 | 38.9 | 0.15 | 1-butene | 96.5 | 88.7 |
| Comparative Example 3 | V3 | 0.46 | 3.73 | 1-butene | 97.1 | 89.0 |

As is apparent from the results in Table 1, in the shaped catalysts (F1) to (F4) produced with the same catalyst ingredient (Mo=12, Bi=1.7, Ni=2.8, Fe=1.8, Co=5.2, K=0.15) while only the relative centrifugal force is changed (Examples 1 to 4), the attrition degree is so small as about 1% at most and thus it is realized that the catalysts have a sufficient practical strength. Moreover, in the reaction test performed using the shaped catalyst (F1) to (F4), good results are obtained in both of the raw material conversion and the yield. On the other hand, in the shaped catalyst (V1) shaped under the condition of a relative centrifugal force of 1 G or less (Comparative Example 1), it is realized that the attrition degree exceeds 3% and thus the catalyst strength is practically insufficient.

Also, in the shaped catalysts (F5) to (F8) prepared with the same catalyst ingredient (Mo=12, Bi=1.7, Fe=2.0, Co=6.75, Ni=1.0, Cs=0.20) using a catalyst ingredient different from that in the above Examples while only the relative centrifugal force is changed (Examples 5 to 8), the attrition degree is less than 1% and thus it is realized that the strength reaches a sufficient practical strength. On the other hand, in the shaped catalyst (V3) shaped under the condition of a relative centrifugal force of 1 G or less (Comparative Example 3), it is realized that the attrition degree exceeds 3% and thus the catalyst strength is practically insufficient.

Moreover, as a result of the oxidation reaction of isobutylene using the shaped catalyst (F5) or the shaped catalyst (F6), good raw material conversion and yield were obtained.

Similarly, as a result of the oxidative dehydrogenation reaction of 1-butene using the shaped catalyst (F7) or the shaped catalyst (F8), good raw material conversion and yield were obtained. However, in the shaped catalyst (V2) shaped under the condition of a relative centrifugal force more than the range of the invention, it is realized that the raw material conversion obviously decreases in the oxidative dehydrogenation reaction of 1-butene carried out under the same conditions.

From the above results, according to the process of the invention, it is apparent that a catalyst having an excellent catalyst strength and showing good reaction results can be produced.

While the invention has been described in detail and with reference to specific embodiments thereof, it will be apparent to one skilled in the art that various changes and modifications can be made therein without departing from the spirit and scope thereof.

The present application is based on Japanese Patent Application No. 2012-098259 filed on Apr. 23, 2012, and the contents are incorporated herein by reference. Also, all the references cited herein are incorporated as a whole.

INDUSTRIAL APPLICABILITY

According to the present invention, it becomes possible to produce a shaped catalyst having both of sufficient mechanical strength and catalytic performance.

The shaped catalyst produced by the process of the invention is useful as a catalyst for producing acrolein and/or acrylic acid from propylene, methacrolein and/or methacrylic acid from isobutylene and/or tertiary-butyl alcohol, or butadiene from n-butene.

The invention claimed is:

1. A process for producing a shaped catalyst for a fixed-bed oxidation reaction or a fixed-bed oxidative dehydrogenation reaction, comprising:
   supporting a catalyst powder containing a complex metal oxide having molybdenum as an essential ingredient on an inert support by a tumbling granulation method at a relative centrifugal force of 1 to 35G,
   wherein the complex metal oxide has a composition represented by the following formula (1):

$Mo_aBi_bNi_cCo_dFe_fX_gY_hO_x$         Formula (1)

wherein Mo, Bi, Ni, Co, Fe and O represents molybdenum, bismuth, nickel, cobalt, iron and oxygen, respectively;
   X represents at least one element selected from the group consisting of tungsten, antimony, tin, zinc, chromium, manganese, magnesium, silicon, aluminum, cerium, tellurium, boron, germanium, zirconium and titanium;
   Y represents at least one element selected from the group consisting of potassium, rubidium, calcium, barium, thallium and cesium;
   a, b, c, d, f, g, h and x represents numbers of atoms of molybdenum, bismuth, nickel, cobalt, iron, X, Y and oxygen, respectively, and a=12, b=0.1 to 7, c+d=0.5 to 20, f=0.5 to 8, g=0 to 2, h=0.005 to 2, and x=a value determined depending on oxidation states of individual elements.

2. The process for producing a shaped catalyst according to claim 1, wherein an attrition degree of the shaped catalyst to be produced is 3% by weight or less.

3. A process for producing butadiene comprising reacting n-butene in an oxidative dehydrogenation reaction in the presence of a shaped catalyst produced according to claim 1.

4. A process for producing an unsaturated aldehyde and/or an unsaturated carboxylic acid comprising reacting an unsaturated hydrocarbon in an oxidation reaction in the presence of a shaped catalyst produced according to claim 1.

* * * * *